US012691205B2

(12) United States Patent
Aelen et al.

(10) Patent No.: US 12,691,205 B2
(45) Date of Patent: Jul. 28, 2026

(54) PUMP ARRANGEMENT, CONFIGURED TO BE USED WITH A DOUBLE BREAST PUMP DEVICE

(71) Applicant: KONINKLIJKE PHILIPS N.V., Eindhoven (NL)

(72) Inventors: Paul Aelen, Eindhoven (NL); Johannes Petrus Antonius Maria Van Asseldonk, Best (NL); Arjan Teodor Van Wieringen, Malden (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1572 days.

(21) Appl. No.: 16/973,470

(22) PCT Filed: Jul. 1, 2019

(86) PCT No.: PCT/EP2019/067512
§ 371 (c)(1),
(2) Date: Dec. 9, 2020

(87) PCT Pub. No.: WO2020/007759
PCT Pub. Date: Jan. 9, 2020

(65) Prior Publication Data
US 2021/0244863 A1 Aug. 12, 2021

(30) Foreign Application Priority Data
Jul. 4, 2018 (EP) ..................................... 18181695

(51) Int. Cl.
| | |
|---|---|
| *A61M 1/06* | (2006.01) |
| *A61M 1/00* | (2006.01) |
| *F04B 9/12* | (2006.01) |

(52) U.S. Cl.
CPC ................ *A61M 1/06* (2013.01); *A61M 1/74* (2021.05); *A61M 1/80* (2021.05); *F04B 9/1207* (2013.01);
(Continued)

(58) Field of Classification Search
CPC ...... A61M 1/06; A61M 1/069; A61M 1/0693; A61M 1/06935; A61M 1/062
See application file for complete search history.

(56) References Cited

U.S. PATENT DOCUMENTS

| | | |
|---|---|---|
| 2004/0133151 A1 | 7/2004 | Watanabe |
| 2013/0123689 A1 | 5/2013 | Bosman |
| 2016/0166745 A1 | 6/2016 | Aalders |

FOREIGN PATENT DOCUMENTS

| | | |
|---|---|---|
| WO | 03092768 | 11/2003 |
| WO | 2015029030 | 3/2015 |
| WO | 2016/179580 | 11/2016 |

OTHER PUBLICATIONS

International Search Report and Written Opinion Dated Sep. 2, 2019 for International Application No. PCT/EP2019/067512 Filed Jul. 1, 2019.

*Primary Examiner* — Emily L Schmidt

(57) ABSTRACT

A pump arrangement (5) for use with a breast pump device comprises a pump element (51), an expression kit air conduit (55) designed to allow for air connection of an expression kit (2) of the device to the pump arrangement (5), a volume element (54) configured to store vacuum in the pump arrangement (5), and a storage switching mechanism (58) arranged between the expression kit air conduit (55) and the volume element (54), configured to switch between a position of direct connection of the expression kit air conduit (55) to the volume element (54) at a bypass position with respect to the pump element (51) and a position of disconnection of the expression kit air conduit (55) from the
(Continued)

volume element (54). Through a direct exchange of vacuum between an expression kit (2) and the volume element (54), support of the functioning of the pump element (51) is realized.

17 Claims, 2 Drawing Sheets

(52) U.S. Cl.
CPC ....... *A61M 1/06935* (2021.05); *A61M 1/0697* (2021.05); *A61M 2205/3337* (2013.01)

PUMP ARRANGEMENT, CONFIGURED TO BE USED WITH A DOUBLE BREAST PUMP DEVICE

CROSS REFERENCE TO RELATED APPLICATIONS

This application is the U.S. National Phase application under 35 U.S.C. § 371 of International Application No. PCT/EP2019/067512 filed Jul. 1, 2019, which claims the benefit of European Patent Application Number 18181695.0 filed Jul. 4, 2018. These applications are hereby incorporated by reference herein.

FIELD OF THE INVENTION

The invention relates to a pump arrangement, configured to be used with a breast pump device comprising an expression kit designed to subject a breast of a user of the device to a pressure profile and to receive milk expressed from the breast, the pump arrangement comprising: a pump element configured to create the pressure profile in the expression kit, a system of air conduits, including an expression kit air conduit designed to allow for air connection of the expression kit to the pump arrangement, and a volume element configured to store vacuum in the pump arrangement.

The invention also relates to a breast pump device, comprising an expression kit designed to subject a breast of a user of the device to a pressure profile and to receive milk expressed from the breast, and a pump arrangement as mentioned.

The invention further relates to a method of operating a pump arrangement of a breast pump device comprising an expression kit designed to subject a breast of a user of the device to a pressure profile and to receive milk expressed from the breast, the pump arrangement comprising a pump element configured to create the pressure profile in the expression kit, an expression kit air conduit designed to allow for air connection of the expression kit to the pump arrangement, and a volume element configured to store vacuum in the pump arrangement.

BACKGROUND OF THE INVENTION

In general, a breast pump device is a well known tool for extracting milk from a breast of a user of the device, i.e. a lactating woman, or from two breasts simultaneously. Breast pump devices may be used in various situations, for example, if a baby or infant is not capable of extracting milk from the breast, or if a mother is separated from her baby or infant and the baby or infant is to be fed with breast milk at a later stage, by the mother or another person. Hence, breast pump devices are used by women to express breast milk at a convenient time, to be stored for later consumption by their/a baby or infant. Breast pump devices may also be helpful in a situation in which it is desired to stimulate and increase milk production in women with a low milk supply or to relieve pressure from engorged breasts.

A breast pump device is typically operated with one or two expression kits. A breast pump device that is designed to enable the use of two expression kits is referred to as double breast pump device. Among other things, an expression kit comprises a breast-receiving funnel for receiving a woman's breast, which funnel may be equipped with pads or the like for massaging the breast in a certain way, and is designed for connection to a vacuum unit for realizing a pressure cycle in the expression kit, by means of which milk expression from the breast is enabled. In practical cases, the vacuum unit comprises an electric vacuum pump element, but manually operated breast pump devices are also known and used in practice. The fact is that by generating a pressure cycle, particularly a vacuum cycle, possibly accompanied by a certain way of massaging the breast, a simulation of a feeding action is obtained, which triggers the necessary let-down reflex in the lactating woman using the breast pump device. For the sake of completeness, it is noted that the term "vacuum" as used in this text refers to a relatively low pressure, i.e. a pressure that is significantly lower than ambient (atmospheric) pressure, and that is also referred to as underpressure. In this respect, it is further noted that creating vacuum is to be understood as involving a decrease of pressure value, and releasing or decreasing vacuum is to be understood as involving an increase of pressure value.

WO 2016/179580 A1 relates to a breast pump system having a vacuum pump element attached to a power source and a microprocessor. Fluidly attached to the suction side of the pump element is a vacuum cylinder. Fluidly attached to the vacuum cylinder is a vent valve. Also attached to the vent valve is a vent with optional silencer and a manifold. In a preferred embodiment, the manifold is a 3-way connector having three attachment ports, wherein one of the attachment ports is fluidly attached to the vent valve. Fluidly attached to a second of the attachment ports is a suction tubing connecting a first port of a suction and milk separator device to the manifold. Fluidly attached to a third of the attachment ports is a milk tubing connecting a second port of the suction and milk separator device to the manifold. A breast-receiving funnel is connected to a third port of the suction and milk separator device. Between the ends of the milk tubing, a milk bottle is arranged, and also an isolation valve that serves for maintaining vacuum in the milk bottle.

In the context of the breast pump system known from WO 2016/179580 A1, the use of a vacuum cylinder allows the use of a smaller, quieter pump element than would otherwise be required. The vacuum cylinder acts as a vacuum storage reservoir and is arranged to receive vacuum directly from the pump element. As the pump element is kept activated throughout the vacuum cycle, the vent valve opens to the manifold and the pump element, and closes the vent, and provides vacuum for the system. When the vent valve closes to the pump element and opens to the vent and the manifold, the system is vented, except for the vacuum cylinder, which is further depressurized by continuous operation of the pump element. When the vent valve is closed to the vent and opened to the manifold and the pump element, the lower pressure in the vacuum cylinder provides a vacuum boost to the system, even with a smaller, quieter pump element, and the pump element is operated continuously rather than being switched on and off.

In the field of breast pump devices, there is always a need for compactness of design and reduction of weight in view of the fact that breast pump devices are more often than not used as portables. Another need is to reduce consumption of electric energy. The present invention is in the context of those particular needs and is therefore aimed at providing a way of downsizing breast pump devices, especially downsizing the pump arrangement of breast pump devices, and/or a way of saving energy.

SUMMARY OF THE INVENTION

According to the invention, a pump arrangement is provided that is configured to be used with a breast pump device comprising an expression kit designed to subject a breast of a user of the device to a pressure profile and to receive milk expressed from the breast.

The pump arrangement comprises:

a pump element configured to create the pressure profile in the expression kit, a system of air conduits, including an expression kit air conduit designed to allow for air connection of the expression kit to the pump arrangement, a volume element configured to store vacuum in the pump arrangement, and a storage switching mechanism arranged between the expression kit air conduit and the volume element, configured to switch between a position of direct connection of the expression kit air conduit to the volume element at a bypass position with respect to the pump element and a position of disconnection of the expression kit air conduit from the volume element.

In the pump arrangement according to the invention, it is possible to make a direct air connection between the expression kit air conduit and the volume element at a bypass position with respect to the pump element, namely by putting a switching mechanism arranged between the expression kit air conduit and the volume element to a position for enabling a direct air connection between the expression kit air conduit and the volume element at a bypass position with respect to the pump element.

The invention is based on the insight that by using a volume element and having a configuration in which the expression kit air conduit can be connected directly to such element, it is possible to reuse vacuum from an expression kit, assuming the intended use of the pump arrangement with a breast pump device. Contrary to what is known from the art, when the invention is applied, not all of the reduced pressure created in the expression kit is continually vented to the environment and therefore lost during the vacuum cycle. The fact is that according to the invention, at least part of the underpressure of the expression kit is transferred to the volume element at the moment in the vacuum cycle that it is needed to release the pressure in the expression kit. In a subsequent step of realizing underpressure in the expression kit, vacuum is not only created by drawing air from the expression kit under the influence of the pump element, but also by moving air from the expression kit to the volume element through direct air communication between the expression kit and the volume element. In this way, the pump element is supported in the function of realizing the vacuum cycle and can be chosen so as to be smaller and cheaper, while electric energy can be saved.

By temporarily storing energy from the expression kit and reusing the energy in the expression kit, it might further be possible to obtain steeper pressure profiles on the basis of the fact that using a volume element as a vacuum buffer allows for generating a sharper reduction of pressure in the expression kit than could be done by only using a pump element. Also, if a battery is used for providing power to the pump element, the lifetime of the battery may be increased and/or the battery may be chosen so as to be smaller. In view of the fact that the pump element is not addressed to the same extent as would be the case in a conventional situation in which all of the vacuum is continually released to the environment, it is to be concluded that application of the invention also may be beneficial to a long lifetime of the pump element. In the context of a double breast pump device, the invention may be applied to eliminate a need for two or more pump elements, because one relatively small pump element may be sufficient for creating the vacuum cycle as desired.

In a practical embodiment of the pump arrangement according to the invention, the volume element comprises an air container having a significantly larger diameter than the air conduits. It may further be practical if the storage switching mechanism comprises a solenoid valve, which is a reliable type of valve that can be accurately controlled.

Besides the storage switching mechanism, the pump arrangement may comprise an environment switching mechanism arranged between the expression kit air conduit and the environment of the pump arrangement, configured to switch between a position of opening the expression kit air conduit to the environment of the pump arrangement and thereby allowing venting of the expression kit, and a position of closing the expression kit air conduit to the environment of the pump arrangement. Like the storage switching mechanism, the environment switching mechanism may comprise a solenoid valve. By using the environment switching mechanism, it is possible to ensure that the expression kit is open or closed to the environment at appropriate moments in the vacuum cycle.

Advantageously, a pump arrangement having both the storage switching mechanism and the environment switching mechanism is equipped with a controller configured to control operation of the pump arrangement according to the following repetitive algorithm of successive steps:

setting a condition of the pump arrangement in which the storage switching mechanism is in a position for disconnecting the expression kit air conduit from the volume element, and the environment switching mechanism is in a position for disconnecting the expression kit air conduit from the environment;

setting a condition of the pump arrangement in which the storage switching mechanism is in a position for connecting the expression kit air conduit to the volume element, and the environment switching mechanism is in a position for disconnecting the expression kit air conduit from the environment;

setting a condition of the pump arrangement in which the storage switching mechanism is in a position for disconnecting the expression kit air conduit from the volume element, and the environment switching mechanism is in a position for connecting the expression kit air conduit to the environment; and setting a condition of the pump arrangement in which the storage switching mechanism is in a position for connecting the expression kit air conduit to the volume element, and the environment switching mechanism is in a position for disconnecting the expression kit air conduit from the environment.

The successive steps as defined in the foregoing can be denoted as being a first step of creating a vacuum in the expression kit under the influence of the pump element, a second step of establishing a short circuit between the expression kit and the volume element, while keeping the expression kit disconnected from the environment, as a result of which the vacuum in the expression kit is released to some extent and a vacuum is created in the volume element to some extent, a third step of further releasing the vacuum in the expression kit by enabling air communication of the expression kit to the environment, and a fourth step of establishing a short circuit between the expression kit and the volume element, as a result of which a vacuum in the expression kit is created to some extent and the vacuum is decreased in the volume element to some extent. The fourth step is followed by the first step in order to further create a vacuum in the expression kit before the situation is turned around again in the second step, etc. The pump element only needs to be operated in the first step.

The pump arrangement according to the invention may be equipped with at least one pressure sensor arranged and configured to determine when the pressure has reached a certain threshold and a switch is to be made from a step in which the storage switching mechanism is in a position for connecting the expression kit air conduit to the volume element to a subsequent step in which the storage switching mechanism is in a position for disconnecting the expression kit air conduit from the volume element. Such a pressure sensor may be part of a general control system of the pump arrangement that comprises the controller as mentioned earlier.

Within the framework of the invention, it is possible for the expression kit air conduit to be directly connected to a suction side of the pump element without application of a switching mechanism. This is not essential, but costs can be saved and reliability can be increased if the number of components of the pump arrangement is kept to a minimum.

In the pump arrangement according to the invention, at least one resistance may be arranged in at least one of the air conduits of the pump arrangement. By having a resistance in an air conduit, it is possible to determine the speed of an airflow through that air conduit, and thus the speed at which pressure can be reduced or increased through the air conduit. The at least one resistance may be controllable so as to allow the extent to which an airflow is resisted to be set according to desire. On the basis thereof, it is possible to offer various modes of operating a breast pump device to a user.

The pump arrangement according to the invention may comprise a connection terminal associated with an end of the expression kit air conduit and being designed to function as a connecting interface between an expression kit and the expression kit air conduit, as one possible way of facilitating the necessary air connection between an expression kit and the pump arrangement. It is very practical if the pump arrangement according to the invention is accommodated in a vacuum unit of a breast pump device comprising an expression kit that is connectable to and disconnectable from the vacuum unit. In such a case, assuming that the pump arrangement comprises the connection terminal as mentioned, the connection terminal may be arranged so as to be accessible at an outside wall of a housing of the vacuum unit.

The volume element may be arranged as an integral part of the pump arrangement, but it is also possible that the volume element is arranged in a module that is connectable to and disconnectable from the pump element and the expression kit air conduit, for example.

The invention also provides a breast pump device, comprising an expression kit designed to subject a breast of a user of the device to a pressure profile and to receive milk expressed from the breast, and a pump arrangement as described in the foregoing. In conformity with what has been indicated earlier, the breast pump device may comprise a vacuum unit, in which case it is practical if the expression kit is connectable to and disconnectable from the vacuum unit, and the pump arrangement is accommodated in the vacuum unit.

The invention further relates to a method of operating a pump arrangement of a breast pump device comprising an expression kit designed to subject a breast of a user of the device to a pressure profile and to receive milk expressed from the breast, the pump arrangement comprising a pump element configured to create the pressure profile in the expression kit, an expression kit air conduit designed to allow for air connection of the expression kit to the pump arrangement, and a volume element configured to store vacuum in the pump arrangement, the expression kit air conduit and the volume element being connectable to and disconnectable from each other directly at a bypass position with respect to the pump element, and the expression kit air conduit being connectable to and disconnectable from the environment of the pump arrangement, the method comprising repeating the following successive steps:

setting a condition of the pump arrangement in which the expression kit air conduit is disconnected from both the volume element and the environment;

setting a condition of the pump arrangement in which the expression kit air conduit is connected to the volume element and disconnected from the environment;

setting a condition of the pump arrangement in which the expression kit air conduit is disconnected from the volume element and connected to the environment;

setting a condition of the pump arrangement in which the expression kit air conduit is connected to the volume element and disconnected from the environment.

As noted earlier, the successive steps as defined in the foregoing can be denoted as being a first step of creating a vacuum in the expression kit under the influence of the pump element, a second step of allowing for direct exchange of air between the expression kit and the volume element, while keeping the expression kit disconnected from the environment, as a result of which the vacuum in the expression kit is released to some extent and a vacuum is created in the volume element to some extent, a third step of further releasing the vacuum in the expression kit, namely by allowing the expression kit to vent to the environment, and a fourth step of allowing for a direct exchange of air between the expression kit and the volume element, as a result of which a vacuum in the expression kit is created to some extent and the vacuum is decreased in the volume element to some extent. The fourth step is followed by the first step in order to further create a vacuum in the expression kit before the situation is turned around again in the second step, etc. The pump element only needs to be operated in the first step.

The above-described and other aspects of the invention will be apparent from and elucidated with reference to the following detailed description of a breast pump device and particularly a pump arrangement of the breast pump device.

BRIEF DESCRIPTION OF THE DRAWINGS

The invention will now be explained in greater detail with reference to the figures, in which equal or similar parts are indicated by the same reference signs, and in which.

DETAILED DESCRIPTION OF EMBODIMENTS

Figure 1:
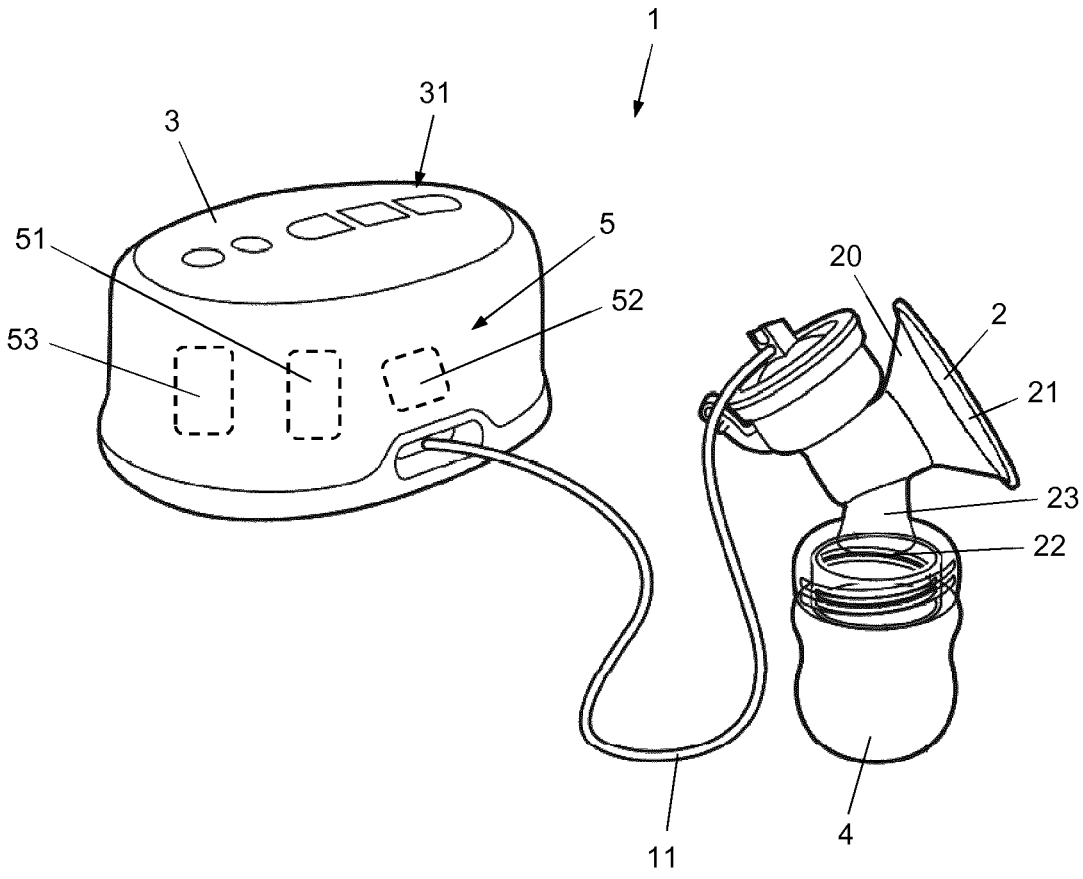
FIG. 1 diagrammatically shows a breast pump device comprising a vacuum unit, an expression kit, and a flexible air hose interconnecting the vacuum unit and the expression kit.

The invention is in the field of breast pump devices, particularly electric breast pump devices. With reference to FIG. 1, a general description of an electric breast pump device will be given so as to generate a clear picture of the context in which the invention is applicable.

The breast pump device 1 comprises at least one expression kit 2 and a vacuum unit 3 for generating a pressure cycle during which vacuum is alternatingly created and released, for which reason the pressure cycle is also referred to as vacuum cycle. The expression kit 2 comprises a functional expression body 20 and a milk receptacle 4 that is connectable to the expression body 20, e.g. by screwing, thereby closing a lower end of the expression body 20.

In FIG. 1, the use of a single expression kit 2 is illustrated, which does not alter the fact that the invention is similarly applicable to the use of two expression kits. In the latter case, it may be so that the two expression kits are both connectable to a single, common vacuum unit. Further, in the latter case, it is possible that a single milk receptacle is used for receiving milk from both expression kits, but it may also be practical to use two separate milk receptacles.

The vacuum unit 3 is an electric vacuum unit and comprises a pump arrangement 5 including an electric pump element 51 and an air valve 52 for realizing the vacuum cycle as mentioned during operation, i.e. during pumping sessions to be performed by means of the breast pump device 1. The pump element 51, the air valve 52 and an associated controller 53 for realizing proper operation of the pump arrangement 5 are designed to function in a manner that is well known in the field of breast pump devices. Therefore, further details of these components will not be further explained in the present text, and the same is applicable to other practical aspects of the vacuum unit 3 known per se. For the same reason, the pump element 51, the air valve 52 and the controller 53 are only diagrammatically depicted in FIG. 1 as dashed rectangles.

The vacuum unit 3 may accommodate a battery or other means for providing electric power to the various components of the vacuum unit 3 during a pumping session. Alternatively or additionally, it is possible for the vacuum unit 3 to be equipped with an electric cord for connection of the vacuum unit 3 to an external source of electric power, which electric cord may be fixed to the vacuum unit 3 or detachably connected to the vacuum unit 3. Further, the vacuum unit 3 may be provided with a user interface 31 for allowing a user of the vacuum unit 3 to influence operational parameters such as suction force, pumping frequency, and variation of the suction force over time. In general, a user interface 31 may be realized in any suitable manner such as through a number of buttons as illustrated in FIG. 1, or through a touch screen, for example.

The expression body 20 of the expression kit 2 comprises a breast-receiving funnel 21, an aperture acting as a milk outlet 22, and a milk path 23 from the breast-receiving funnel 21 to the milk outlet 22. The breast-receiving funnel 21 is thus in fluid communication with the milk outlet 22 through the milk path 23. The breast-receiving funnel 21 can comprise a massage cushion or the like (not shown) for providing a soft and warm feel to the breast and/or imitating a baby's sucking action.

In FIG. 1, the breast pump device 1 is shown in an assembled condition, in which the vacuum unit 3 is connected to the expression kit 2 through a flexible air hose 11. Such a configuration allows for a remote arrangement of the vacuum unit 3 with respect to the expression kit 2, so that the size of that part of the breast pump device 1 that is to be applied to a user's breast can be kept within reasonable limits.

In general, the breast pump device 1 is used to realize milk expression from a woman's breast. To that end, an alternating vacuum (vacuum cycle) is applied to the breast, wherein a sequence of generating underpressure in the expression kit 2 under the influence of the pump element 51 and releasing the underpressure from the expression kit 2 is continuously repeated. During periods of low pressure, or vacuum, the actual process in which milk is expressed from the breast takes place. Every time that the vacuum is released and the pressure prevailing in the expression kit 2 increases, freshly expressed milk drops in the milk receptacle 4.

Figure 2:
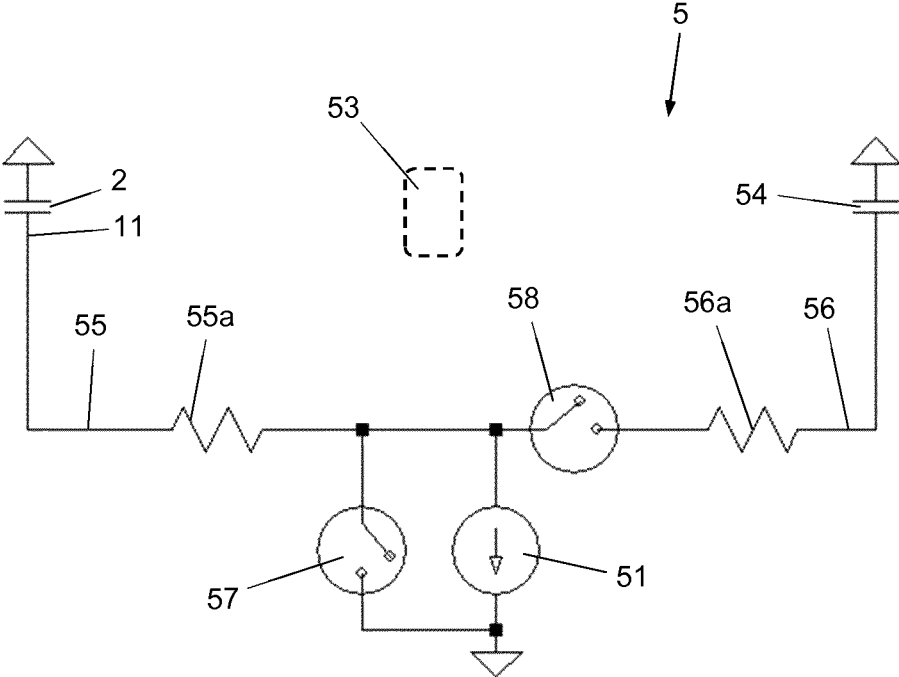
FIG. 2 is a schematic of the set-up of a pump arrangement according to the invention, as may be used in a breast pump device, and further diagrammatically shows an expression kit connected to the pump arrangement.

FIG. 2 serves to illustrate the set-up of a pump arrangement 5 according to the invention, as may be used in a breast pump device 1. Besides providing a diagrammatic representation of components of the pump arrangement 5 and their positioning with respect to each other, FIG. 2 further illustrates an expression kit 2 connected to the pump arrangement 5.

Besides a pump element 51 that is intended to create a pressure profile as desired in the expression kit 2, and a controller 53 that is configured to control operation of the pump arrangement 5, the pump arrangement 5 comprises an air container 54, a system of air conduits 55, 56 and two switching mechanisms 57, 58 as will now be explained. In respect of the pump element 51, it is noted that as is usual in the field of pump elements used for displacing air, the pump element 51 has a suction side where air is let in to the pump element 51 during operation of the pump element 51 and a discharge side where air is discharged from the pump element 51 during operation of the pump element 51. The pump element 51 is enabled when power is supplied to the pump element 51, and, consequently, the pump element 51 is disabled when the power is cut off.

The pump arrangement 5 according to the invention comprises an expression kit air conduit 55 that is designed to allow for air connection of an expression kit 2 to the pump arrangement 5. In a practical situation, assuming that the pump arrangement 5 is located in a vacuum unit 3, the expression kit air conduit 55 of the pump arrangement 5 extends inward from a connecting interface that is accessible at the outside of the vacuum unit 3 and that is designed to enable the flexible air hose 11 extending from the expression kit 2 to be interconnected with the expression kit air conduit 55. The expression kit air conduit 55 is connectable to and disconnectable from the environment of the pump arrangement 5 through an environment switching mechanism 57, i.e. from an area where ambient pressure is prevailing. Hence, the expression kit 2 to be interconnected with the expression kit air conduit 55 can be vented through the environment switching mechanism 57, namely when the environment switching mechanism 57 is in a position of connecting the expression kit air conduit 55 to the environment.

The pump arrangement 5 according to the invention further comprises a storage air conduit 56 that extends from the air container 54 and that is connectable to and disconnectable from the expression kit air conduit 55 through a storage switching mechanism 58. In a general sense, according to an important aspect of the invention, a means or mechanism is provided for enabling a direct connection between the expression kit air conduit 55 and the storage air conduit 56, as a kind of short circuit between the air conduits 55, 56 at a bypass position with respect to the pump element 51, so as to realize a direct exchange of air between the air conduits 55, 56 and thereby between the expression kit 2 and the air container 54 when appropriate during operation of the breast pump device 1.

On the basis of the design of the pump arrangement 5 with the storage switching mechanism 58, it is possible to realize different air paths through the pump arrangement 5, depending on the settings of the storage switching mechanism 58. A practical way of controlling the pump arrangement 5 during operation thereof involves a repetition of the following four successive steps:

1) having the environment switching mechanism 57 and the storage switching mechanism 58 in an air flow blocking position, so that the pressure in the expression kit 2 may be reduced under the influence of the pump element 51, 2) having the storage switching mechanism 58 in an air flow enabling position while still having the environment switching mechanism 57 in an air flow blocking position, so that direct air exchange between the expression kit air conduit 55 and the storage air conduit 56 is possible and the pressures prevailing in the expression kit 2 and the air container 54 are automatically adjusted without needing to address the pump element 51, wherein the pressure in the expression kit 2 increases and the pressure in the air container 54 decreases, 3) having the environment switching mechanism 57 in an air flow enabling position while having the storage switching mechanism 58 in an air flow blocking position, so that the pressure in the expression kit 2 may be further increased as a result of the fact that the expression kit 2 is vented to the environment, and 4) having the storage switching mechanism 58 in an air flow enabling position while having the environment switching mechanism 57 in an air flow blocking position, as is the case in the second step, so that direct air exchange between the expression kit 2 and the air container 54 is possible and the pressures prevailing in the expression kit 2 and the air container 54 are automatically adjusted without needing to address the pump element 51, wherein the pressure in the expression kit 2 decreases and the pressure in the air container 54 increases.

It is possible for the pump arrangement 5 to be equipped with at least one pressure sensor for determining when the pressure has reached a certain threshold such that a switch can be made from the step of transferring vacuum from the expression kit 2 to the air container 54 to the subsequent step, i.e. from the second step to the third step in the above listing of steps, and also when the pressure has reached a certain threshold such that a switch can be made from the step of precharging the expression kit 2 with vacuum from the air container 54 to the subsequent step, i.e. from the fourth step to the first step in the above listing of steps. Alternatively, it is possible to apply open loop control and to automatically make switches on the basis of preset parameters. Further, one or more resistances may be added to one or more air conduits of the pump arrangement 5. By way of example, FIG. 2 illustrates the use of a resistance 55*a* in the expression kit air conduit 55, and also the use of a resistance 56*a* in the storage air conduit 56. By having one or more resistances in an air conduit, it is achieved that a speed at which pressure is reduced or released in the expression kit 2 can be influenced. In a sophisticated embodiment of the pump arrangement 5, the one or more resistances may be controllable.

When the above sequence is followed, it is achieved that every time it is intended to address the expression kit 2 for the purpose of creating a vacuum, the operation of the pump element 51 is supported on the basis of the fact that pressure reduction in the expression kit 2 is already realized to some extent as a result of a preceding step that involves establishing a direct connection between the expression kit air conduit 55 and the storage air conduit 56 to which the expression kit 2 and the air container 54, respectively, are connected. The energy provided by the pump element 51 is very efficiently used on the basis of this fact that an operational sequence aimed at reusing vacuum from the expression kit 2 is continually repeated, wherein the air container 54 is a volume element serving as a space, particularly a vacuum buffer, that is arranged and configured to receive and store vacuum from the expression kit 2 during one period of the vacuum cycle, and to allow transfer of vacuum to the expression kit 2 during another period of the vacuum cycle. As one of the important advantageous results of this way of doing, it is possible to use a relatively small pump element 51 in the pump arrangement 5. In this way, space, energy and costs can be saved.

At the end of a pumping session, both the environment switching mechanism 57 and the storage switching mechanism 58 are put to an air flow enabling position so that both the expression kit 2 and the air container 54 are allowed to reach ambient pressure.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

As already suggested in the foregoing, the invention is applicable to both the use of a single expression kit 2 and the use of two expression kits 2 with a pump arrangement 5 that is configured to allow reuse of vacuum from the expression kit(s) 2. In a pump arrangement 5 that is suitable for use with two expression kits 2, two volume elements 54 may be present, one for association with one of the expression kits 2, and another for association with another of the expression kits 2. However, in such a pump arrangement 5, it is also possible that a single volume element 54 is provided that is arranged and configured to receive vacuum from two expression kits 2 and to transfer vacuum to two expression kits 2.

A possible summary of the invention reads as follows. A pump arrangement 5 for use with a breast pump device 1 comprises a pump element 51 configured to create a pressure profile in an expression kit 2 of the device 1, a system of air conduits 55, 56, including an expression kit air conduit 55 designed to allow for air connection of the expression kit 2 to the pump arrangement 5, a volume element 54 configured to store vacuum in the pump arrangement 5, and a storage switching mechanism 58 arranged between the expression kit air conduit 55 and the volume element 54, configured to switch between a position of direct connection of the expression kit air conduit 55 to the volume element 54 at a bypass position with respect to the pump element 51 and a position of disconnection of the expression kit air conduit 55 from the volume element 54. In this configuration, it is possible to directly exchange vacuum between an expression kit 2 and the volume element 54, whereby the functioning of the pump element 51 is supported as vacuum from the expression kit 2 is not simply released to the environment but is reused to charge the expression kit 2 with vacuum at the appropriate time in the pressure profile. Among other things, the pump element 51 can be chosen to be smaller than as would be necessary without the presence of the volume element 54 and the possibility of establishing a direct air connection between the expression kit air conduit 55 and the volume element 54.

The invention claimed is:

1. A pump arrangement, configured to be used with an expression kit designed to subject a breast of a user to a pressure profile and to receive milk expressed from the breast, the pump arrangement comprising:

a pump element configured to create the pressure profile in the expression kit;

an expression kit air conduit configured to allow for air connection of the expression kit to the pump arrangement;

a volume element configured to store vacuum in the pump arrangement; and a storage switching mechanism arranged between the expression kit air conduit and the volume element, wherein the storage switching mechanism is configured to switch between a position of direct connection for connecting the expression kit air conduit to the volume element, bypassing the pump element, and a position of disconnection for disconnecting each of the expression kit air conduit and the pump element from the volume element.

2. The pump arrangement according to claim 1, wherein the volume element comprises an air container having a larger diameter than the expression kit air conduit.

3. The pump arrangement according to claim 1, wherein the storage switching mechanism comprises a solenoid valve.

4. The pump arrangement according to claim 1, further comprising:

an environment switching mechanism arranged between the expression kit air conduit and an environment of the pump arrangement, wherein the environment switching mechanism is configured to switch between a position of connection for connecting the expression kit air conduit to the environment of the pump arrangement and a position of disconnection for disconnecting the expression kit air conduit from the environment of the pump arrangement.

5. The pump arrangement according to claim 4, comprising a controller configured to control operation of the pump arrangement by repeating the following successive steps:

setting a condition of the pump arrangement in which the storage switching mechanism is in the position of disconnection for disconnecting the expression kit air conduit from the volume element, and the environment switching mechanism is in the position of disconnection for disconnecting the expression kit air conduit from the environment;

setting a condition of the pump arrangement in which the storage switching mechanism is in the position of direct connection for connecting the expression kit air conduit to the volume element, and the environment switching mechanism is in the position of disconnection for disconnecting the expression kit air conduit from the environment;

setting a condition of the pump arrangement in which the storage switching mechanism is in the position of disconnection for disconnecting the expression kit air conduit from the volume element, and the environment switching mechanism is in the position of connection for connecting the expression kit air conduit to the environment; and setting a condition of the pump arrangement in which the storage switching mechanism is in the position of direct connection for connecting the expression kit air conduit to the volume element, and the environment switching mechanism is in the position of disconnection for disconnecting the expression kit air conduit from the environment.

6. The pump arrangement according to claim 5, further comprising:

at least one pressure sensor arranged and configured to determine when pressure has reached a certain threshold and a switch is to be made from a step in which the storage switching mechanism is in a position for connecting the expression kit air conduit to the volume element to a subsequent step in which the storage switching mechanism is in a position for disconnecting the expression kit air conduit from the volume element.

7. The pump arrangement according to claim 4, wherein the expression kit air conduit is directly connected to a suction side of the pump element without application of a switching mechanism.

8. The pump arrangement according to claim 4, wherein the environment switching mechanism comprises a solenoid valve.

9. The pump arrangement according to claim 1, wherein at least one resistance is arranged in the expression kit air conduit.

10. The pump arrangement according to claim 1, wherein the volume element is arranged as an integral part of the pump arrangement.

11. The pump arrangement according to claim 1, wherein the volume element is arranged in a module that is connectable to and disconnectable from the pump element and the expression kit air conduit.

12. The pump arrangement according to claim 1, wherein the pump arrangement is accommodated in a vacuum unit of a breast pump device comprising the expression kit, wherein the expression kit is connectable to and disconnectable from the vacuum unit.

13. A breast pump device, comprising:

an expression kit designed to subject a breast of a user of the breast pump device to a pressure profile and to receive milk expressed from the breast; and a pump arrangement comprising:

a pump element configured to create the pressure profile in the expression kit;

an expression kit air conduit configured to allow for air connection of the expression kit to the pump arrangement;

a volume element configured to store vacuum; and a storage switching mechanism arranged between the expression kit air conduit and the volume element, wherein the storage switching mechanism is configured to switch between a position of direct connection for connecting the expression kit air conduit to the volume element, bypassing the pump element, and a position of disconnection for disconnecting each of the expression kit air conduit and the pump element from the volume element.

14. The breast pump device according to claim 13, further comprising a vacuum unit, wherein the expression kit is connectable to and disconnectable from the vacuum unit, and the pump arrangement is accommodated in the vacuum unit.

15. The breast pump device according to claim 13, wherein the volume element comprises an air container having a larger diameter than the expression kit air conduit.

16. The breast pump device according to claim 13, wherein the storage switching mechanism comprises a solenoid valve.

17. The breast pump device according to claim 13, wherein the pump arrangement further comprises:

an environment switching mechanism arranged between the expression kit air conduit and an environment of the pump arrangement, wherein the environment switching mechanism is configured to switch between a position of connection for connecting the expression kit air conduit to the environment of the pump arrangement and a position of disconnection for disconnecting the expression kit air conduit from the environment of the pump arrangement.

* * * * *